(12) United States Patent
Baldauf et al.

(10) Patent No.: US 9,921,181 B2
(45) Date of Patent: Mar. 20, 2018

(54) DETECTION OF TRANSLOCATION EVENTS USING GRAPHENE-BASED NANOPORE ASSEMBLIES

(71) Applicant: International Business Machines Corporation, Armonk, NY (US)

(72) Inventors: Julia S. Baldauf, South Melbourne (AU); Matthew Downton, Carlton (AU); Natalie Gunn, Eltham (AU); Stefan Harrer, Hampton (AU); Sridhar Kannam, Hawthorne (AU); Christine Schieber, Southbank (AU); John M. Wagner, Carlton (AU)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 333 days.

(21) Appl. No.: 14/454,704

(22) Filed: Aug. 7, 2014

(65) Prior Publication Data
US 2015/0377830 A1    Dec. 31, 2015

Related U.S. Application Data

(60) Provisional application No. 62/017,504, filed on Jun. 26, 2014.

(51) Int. Cl.
*G01N 27/447* (2006.01)
*C12Q 1/68* (2018.01)
*G01N 33/487* (2006.01)

(52) U.S. Cl.
CPC ..... *G01N 27/44791* (2013.01); *C12Q 1/6827* (2013.01); *G01N 33/48721* (2013.01)

(58) Field of Classification Search
CPC .................................................. G01N 33/48721
See application file for complete search history.

(56) References Cited

U.S. PATENT DOCUMENTS

| 5,397,695 A | 3/1995 | Sutton et al. |
| 6,428,959 B1 | 8/2002 | Deamer |

(Continued)

FOREIGN PATENT DOCUMENTS

| CN | 101516512 A | 8/2009 | |
| CN | 101986145 A * | 3/2011 | ............. G01N 27/00 |

(Continued)

OTHER PUBLICATIONS

EPO computer-generated Englsih language translation of Chen et al. CN 101986145 A, downloaded Dec. 7, 2016.*

(Continued)

*Primary Examiner* — Alexander S Noguerola
(74) *Attorney, Agent, or Firm* — Louis J. Percello; Otterstedt, Ellenbogen & Kammer, LLP

(57) ABSTRACT

Translocation events are sensed using composite nanopore assemblies including nanopores formed in graphene sheets. Single molecule detection and characterization and multi-molecule characterization and identification are provided using such assemblies. Multiple electrodes associated with nanofluidic sensors facilitate detection of ionic current through a nanopore as well as tunneling currents. Current signals of individual molecules are estimated from the combination of an ionic current signal through the nanopore and tunneling current signals obtained at specific locations within the nanopore.

19 Claims, 13 Drawing Sheets

(56) References Cited

U.S. PATENT DOCUMENTS

| | | |
|---|---|---|
| 6,627,067 B1 | 9/2003 | Branton et al. |
| 7,625,469 B1 | 12/2009 | Yelton et al. |
| 7,846,656 B2 | 12/2010 | Mirzabekov et al. |
| 8,003,319 B2 | 8/2011 | Polonsky |
| 8,105,471 B1 | 1/2012 | Han et al. |
| 8,232,105 B1 | 7/2012 | Scott |
| 8,247,238 B2 | 8/2012 | Meinhart et al. |
| 8,262,879 B2 | 9/2012 | Oliver |
| 8,278,055 B2 | 10/2012 | Su et al. |
| 8,388,908 B2 | 3/2013 | Blaga et al. |
| 8,395,901 B2 | 3/2013 | Tour et al. |
| 8,425,745 B2 | 4/2013 | Briman et al. |
| 8,481,334 B1 | 7/2013 | Saul |
| 8,906,609 B1 | 12/2014 | Smirnov et al. |
| 8,968,545 B2 | 3/2015 | Holt |
| 9,255,321 B2 | 2/2016 | Baldauf et al. |
| 9,297,062 B2 | 3/2016 | Baldauf et al. |
| 9,303,310 B2 | 4/2016 | Baldauf et al. |
| 9,309,590 B2 | 4/2016 | Baldauf et al. |
| 2003/0040173 A1 | 2/2003 | Fonash et al. |
| 2004/0144658 A1 | 7/2004 | Flory |
| 2004/0202994 A1 | 10/2004 | Timperman |
| 2005/0221333 A1 | 10/2005 | Sundararajan et al. |
| 2006/0019247 A1 | 1/2006 | Su et al. |
| 2006/0141469 A1 | 6/2006 | Rossier et al. |
| 2006/0231419 A1 | 10/2006 | Barth et al. |
| 2006/0275778 A1 | 12/2006 | Wu et al. |
| 2007/0138132 A1 | 6/2007 | Barth |
| 2008/0003512 A1 | 1/2008 | Kobayashi et al. |
| 2008/0003571 A1 | 1/2008 | McKernan et al. |
| 2008/0067056 A1 | 3/2008 | Searson et al. |
| 2008/0073512 A1 | 3/2008 | Siuzdak et al. |
| 2009/0136948 A1 | 5/2009 | Han et al. |
| 2009/0305273 A1 | 12/2009 | Cao et al. |
| 2010/0009872 A1 | 1/2010 | Eid et al. |
| 2010/0028681 A1 | 2/2010 | Dai et al. |
| 2010/0151454 A1 | 6/2010 | Sundararajan et al. |
| 2011/0053284 A1 | 3/2011 | Meller et al. |
| 2011/0133255 A1 | 6/2011 | Merz |
| 2011/0168562 A1 | 7/2011 | Nuckolls et al. |
| 2011/0236984 A1 | 9/2011 | Sun et al. |
| 2012/0088315 A1 | 4/2012 | Merelle et al. |
| 2012/0193231 A1 | 8/2012 | Afzali-Ardakani et al. |
| 2012/0193237 A1* | 8/2012 | Afzali-Ardakani .... B82Y 15/00 204/627 |
| 2012/0194813 A1 | 8/2012 | Tzeng et al. |
| 2012/0222958 A1 | 9/2012 | Pourmand et al. |
| 2012/0256281 A1 | 10/2012 | Harrer et al. |
| 2013/0037410 A1 | 2/2013 | Xu et al. |
| 2013/0068623 A1 | 3/2013 | Jaramillo-Botero et al. |
| 2013/0085680 A1 | 4/2013 | Arlen et al. |
| 2013/0186758 A1 | 7/2013 | Saha et al. |
| 2013/0256137 A1 | 10/2013 | Holt |
| 2013/0256139 A1 | 10/2013 | Peng |
| 2013/0256154 A1 | 10/2013 | Peng |
| 2013/0264219 A1 | 10/2013 | Afzali-Ardakani |
| 2013/0270521 A1 | 10/2013 | Peng et al. |
| 2014/0045270 A1 | 2/2014 | Shim et al. |
| 2014/0106472 A1 | 4/2014 | Ervin et al. |
| 2014/0206101 A1 | 7/2014 | Liu et al. |
| 2015/0010935 A1 | 1/2015 | Lindsay et al. |
| 2015/0225838 A1 | 8/2015 | Baldauf et al. |

FOREIGN PATENT DOCUMENTS

| | | | |
|---|---|---|---|
| CN | 102621122 A | 8/2012 | |
| JP | 2013090576 A | 5/2013 | |
| KR | 20120000343 A * | 1/2012 | ............ G01N 27/414 |
| WO | WO01027610 | 4/2001 | |
| WO | WO2012160584 A1 | 11/2012 | |
| WO | WO2013011879 A1 | 1/2013 | |
| WO | WO2013016139 A1 | 1/2013 | |
| WO | WO2013016486 A1 | 1/2013 | |
| WO | WO2013116509 A1 | 8/2013 | |
| WO | WO2015057307 A1 | 4/2015 | |
| WO | WO2015057388 A1 | 4/2015 | |

OTHER PUBLICATIONS

Korean Intellectual Property Office computer-generated Englsih language translation of Gi-Beom Kim 1020120000343 A, downloaded Dec. 7, 2016.*

Sadeghi et al., "Graphene Sculpturene Nanopores for DNA Nucleobase Sensing," J. Phys. Chem. 8, May 21, 2014, 118, 6908-6914.*

Nelson et al., "Detection of Nucleic Acids with Graphene Nanopores: Ab Initio Characterization of a Novel Sequencing Device," Nano Lett. 2010, 10, 3237-3242.*

H. Bayley et al., "Stochastic sensors inspired by biology," Nature, vol. 413, No. 6852, 2001, pp. 226-230.

R. Wei et al., "Stochastic sensing of proteins with receptor-modified solid-state nanopores," Nature Nanotechnology, vol. 7, No. 4. 2012, pp. 257-263.

Q. Xu et al., "Controllable atomic scale patterning of freestanding monolayer graphene at elevated temperature," ACS Nano, vol. 7, No. 2, 2013, pp. 1566-1572.

G. F. Schneider et al., "Tailoring the hydrophobicity of graphene for its use as nanopores for DNA translocation," Nature Communications, vol. 4, 2013, 7 pages.

Venkatesan, Bala Murali et al., "Stacked Graphene-A1203 Nanopore Sensors for Sensitive Detection of DNA and DNA-Protein Complexes", ACS Nano, vol. 6, No. 1, 2012, pp. 441-450.

Georgakilas, Vasilios et al., "Functionalization of Graphene: Covalent and Non-Covalent Approaches, Derivatives and Applications", Chemical Reviews 2012, 112, pp. 6156-6214.

Lindsay, Stuart et al., "Recognition Tunnelling", 2010 Nanotechnology 21 262001, doi 10.1088/0957-4484/21/26/262001.

I. Braslavsky, et al., "Sequence Information Can Be Obtained From Single DNA Molecules," Department of Applied Physics, California Institute of Technology; PNAS Apr. 1, 2003; vol. 100; No. 7; pp. 3960-3964.

D. Branton, et al., "The Potential and Challenges of Nanopore Sequencing," Nature Biotechnology; 2008 Nature Publishing Group; pp. 1146-1153.

F. Collins, et al., "The Human Genome Project: Lessons from Large-Scale Biology," Apr. 11, 2003 vol. 300 Science www.sciencemag.org; pp. 286-290.

M. Fedurco, et al., "BTA, a Novel Reagent for DNA Attachment on Glass and Efficient Generation of Solid-Phase Amplified DNA Colonies," Nucleic Acids Research, 2006, vol. 34, No. 3; Published on line Feb. 9, 2006; pp. 1-13.

S. Harrer, et al., "Electrochemical Characterization of Thin Film Electrodes Toward Developing a DNA Transistor," Langmuir Article 2010 American Chemical Society; Langmuir 2010, 26(24), pp. 19191-19198.

T. Harris, et al., "Single-Molecule DNA Sequencing of a Viral Genome," Science vol. 320, 106 (2008); pp. 106-109.

J. Kasianowicz, et al., "Characterization of Individual Polynucleotide Molecules Using a Membrane Channel," Proc. Natl. Acad. Sci. USA; vol. 93; pp. 13770-13773; Nov. 1996 Biophysics.

B. Luan, et al., "Tribological Effects on DNA Translocation in a Nanochannel Coated with a Self-Assembled Monolayer," J. Phys. Chem B., 2010, 114, pp. 17172-17176.

B. Luan, et al., "Base-by-Base Ratcheting of Single Stranded DNA Through a Solid-State Nanopore," Physical Review Letters 104, 238103 (2010); pp. 238103-1-238103-4.

B. Luan, et al., "Control and Reversal of the Electrophoretic Force on DNA in a Charged Nanopore," J. Phys.: Condens. Matter 22 (2010) 454123 (cover plus pp. 1-5).

M. Margulies, et al., "Genome Sequencing in Microfabricated High-Density Picolitre Reactors," Nature vol. 437; Sep. 15, 2005 pp. 376-380.

S. Polonsky, et al., "Nanopore in Metal-Dielectric Sandwich for DNA Position Control," Applied Physics Letters 91, 153103 (2007); pp. 153103-1-153103-3.

(56) References Cited

OTHER PUBLICATIONS

F. Sanger, et al., "DNA Sequencing with Chain-Terminating Inhibitors," Proc. Natl. Acad. Sci. USA; vol. 74, No. 12; pp. 5463-5467; Dec. 1977 Biochemistry.

D. Scott, et al., "Direct Molecular Evolution of Detergent-Stable G Protein-Coupled Using Polymers Encapsulated Cells," 2012 Elsevier Ltd., J. Mal. Biol. (2013) 425, pp. 662-677.

J. SH Endure, et al., "Accurate Multiplex Polony Sequencing of an Evolved Bacterial Genome," Science 309, 1728 (2005); pp. 1728-1732.

G. Turcatti, et al., "A New Class of Cleavable Fluorescent Nucleotides: Synthesis and Optimization as Reversible Terminators for DNA Sequencing by Synthesis," Nucleic Acids Research, 2008, vol. 36, No. 4; Published on line 7 Feb. 2008; pp. 1-13.

D. Wang, et al., "DNA-Translocation Through a Solid State Nanopore coated with a Functionally Switchable Self-Assembled Monolayer," IBM T. J. Watson Research Center, Yorktown Heights, NY USA; 2012; pp. 1-18.

D. Wang, et al., "Regulating the Transport of DNA through Biofriendly Nanochannels in a Thin Solid Membrane," IBM Research at T.J. Watson Center, Yorktown Heights, NY USA; pp. 1-23; Feb. 5, 2014.

E. Yusko, et al., "Developing Nanopores with Fluid Walls for Improved, Single-Molecule Biosensors," Abstract only Feb. 2012; 1 page.

Bayley, Hagan et al.; Stochastic Sensors Inspired by Biology; Nature; vol. 413; p. 226-230; Sep. 13, 2001.

Hickman, James J., et al.; "Toward Orthogonal Self-Assembly of Redox Active Molecules on Pt and Au: Selective Reaction of Disulfide with Au and Isocyanide with Pt"; Langmuir; vol. 8; 357-359; 1992.

Li, Zhiyong, et al.; "Self-Assembly of Alkanethiol Molecules onto Platinum and Platinum Oxide Surfaces"; Langmuir; vol. 19; p. 6744-6749; 2003.

Martin, Benjamin R., et al; "Orthogonal Self-Assembly on Colloidal Gold-Platinum Nanorods"; Advanced Materials; vol. 11, No. 12; p. 1021-1025; 1999.

Miles, Benjamin N., et al.; "Single Molecule Sensing with Solid-State Nanopores: Novel Materials, Methods, and Applications"; Chemical Society Reviews; vol. 42; No. 1; p. 15-28; Jan. 7, 2013.

Petrovykh, Dmitri Y., et al.; Alkanethiols on Platinum: Multicomponent Self-Assembled Monolayers; Langmuir; vol. 22; p. 2578-2587; 2006.

Raillon, C., et al.; "Fast and Automatic Processing of Multi-Level Events in Nanopore Translocation Experiments"; Nanoscale; vol. 4; p. 4916-4924; 2012.

Randolph, S. J., et al.; "Focused, Nanoscale Electron-Beam-Induced Deposition and Etching"; Critical Reviews in Solid State and Materials Sciences; vol. 31; p. 55-89; 2006.

Schoch et al., "Transport Phenomena in Nanofluidics," Reviews of Modern Physics, vol. 80, Jul.-Sep. 2008, 45 pages.

Tabard-Cassa, Vincent, et al.; "Noise Analysis and Reduction in Solid-State Nanopores"; Nanotechnology; vol. 18; p. 1-7; 2007.

Wei, Ruoshan, et al.; "Stochastic Sensing of Proteins with Receptor-Modified Solid-State Nanopores" Nature Nanotechnology; vol. 7; p. 257-263; Apr. 2012.

Authorized Officer Lee W. Young, USPTO as ISA, International Search Report and Written Opinion dated Jan. 22, 2015 for Application No. PCT/US2014/50644, pp. 1-9.

Liu, Changlu, et al.; "Relaxin-3/Insulin-Like Peptide 5 Chimeric Peptide, a Selective Ligand for G Protein-Coupled Receptor (GPCR)135 and GPCR142 over Leucine-Rich Repeat-Containing G Protein-Coupled Receptor 7"; Molecular D Pharmacology; vol. 67, No. 1; p. 231-240; 2005.

Danelon, Christophe, et al.; "Fabrication and Functionalization of Nanochannels by Electron-Beam-Induced Silicon Oxide Deposition"; Langmuir; vol. 22; p. 10711-10715; 2006.

Hou, Xu, et al.; "Building Bio-Inspired Artificial Functional Nanochannels: From Symmetric to Asymmetric Modification"; Angew. Chem. Int. Ed.; vol. 51; p. 5296-5307; 2012.

Authorized Officer Blaine R. Copenheaver, USPTO as ISA, International Search Report and Written Opinion dated Dec. 18, 2014 for Application No. PCT/US2014/052481, pp. 1-11.

Authorized Officer Blaine R. Copenheaver, USPTO as ISA, International Search Report and Written Opinion dated Dec. 29, 2014 for Application No. PCT/US2014/058531, pp. 1-10.

Harrer, S. et al., "Electrochemical Protection of Thin Film Electrodes in Solid State Nanopores," Nanotechnology 22 (2011) 275304, NIH Public Access PDF pp. 1-13.

Paul J. Otterstedt, List of IBM Patents or Patent Applications Treated as Related, pp. 1-2, Sep. 16, 2017.

\* cited by examiner

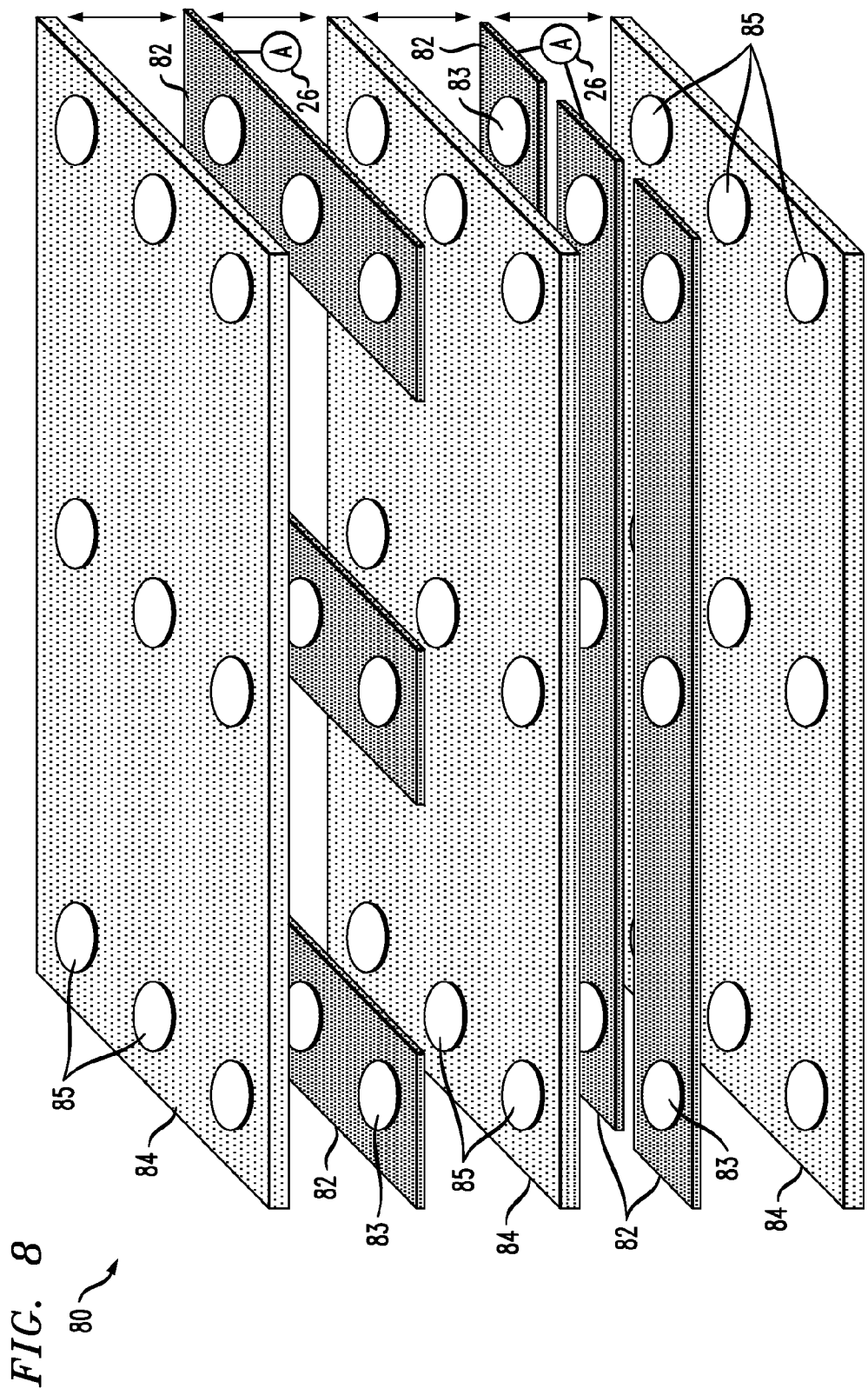

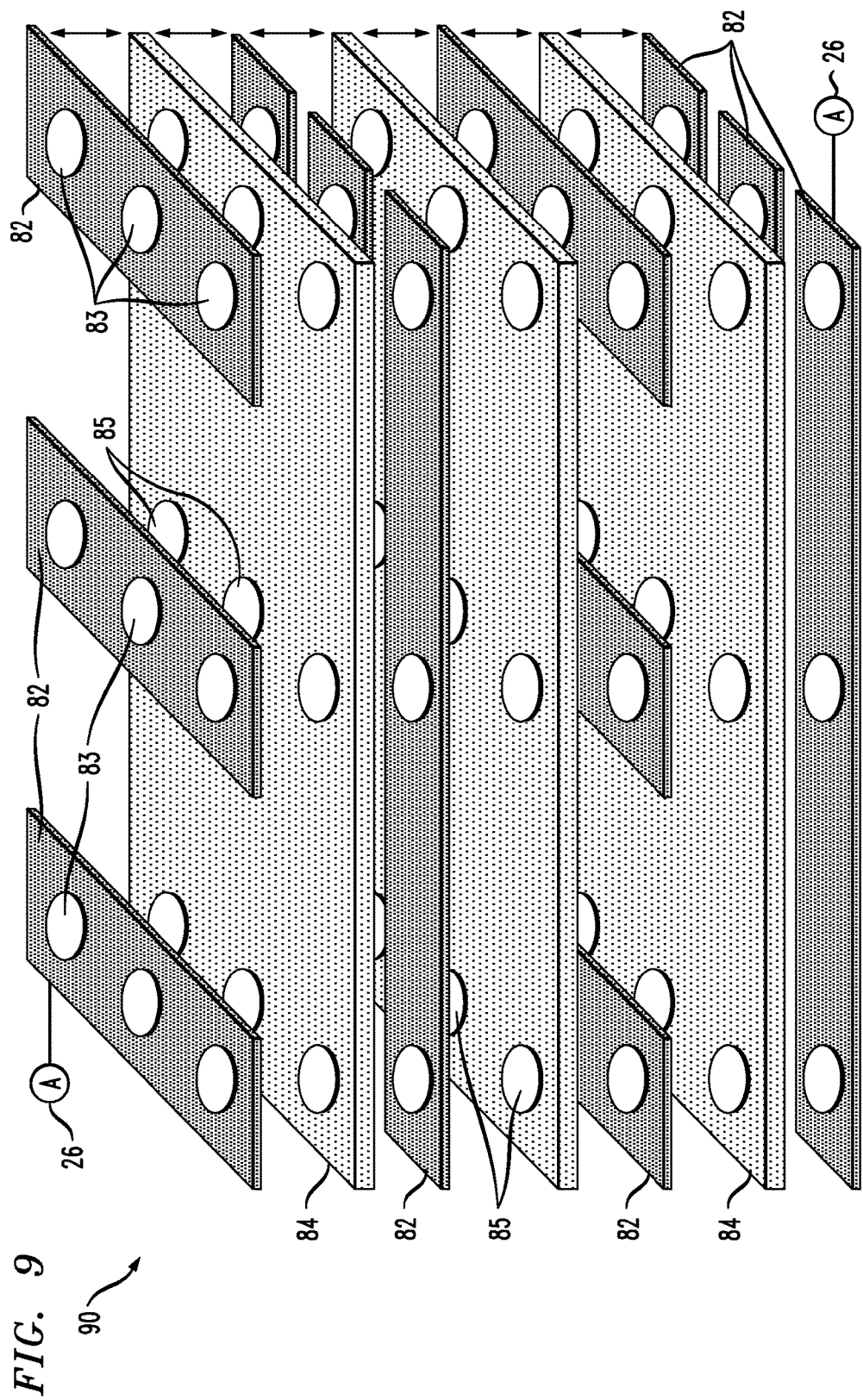

DETECTION OF TRANSLOCATION EVENTS USING GRAPHENE-BASED NANOPORE ASSEMBLIES

CROSS-REFERENCE TO RELATED APPLICATION

This patent application claims the benefit of U.S. Provisional Patent Application Ser. No. 62/017,504 filed on Jun. 26, 2014, and entitled "DETECTION OF TRANSLOCATION EVENTS USING GRAPHENE-BASED NANOPORE ASSEMBLIES." The disclosure of the aforementioned Provisional Patent Application Ser. No. 62/017,504 is expressly incorporated herein by reference in its entirety for all purposes.

FIELD

The present disclosure generally relates to graphene-based nanopore devices, fabrication of such nanopore devices, and methods for detecting translocation events using the graphene-based nanopore devices.

BACKGROUND

Nanoscale fluidic devices include pores and/or channels formed in selected substrates. A solid-state (non-biological) nanopore may be fabricated through TEM (transmission electron microscope) drilling through a selected substrate. Solid-state nanopores can be used to analyze biological proteins. Nanofluidic channels may be fabricated by serial electron beam lithography in order to reach the desired dimensions. Channels can also be fabricated using photolithography, nanoimprint lithography and nanotransfer lithography.

Nanopores have been used as sensors for molecules such as DNA. A small passage may be arranged to separate two electrolyte-filled reservoirs, at least one of which contains target molecules. The target molecules can be drawn through the passage and their presence detected as a drop in current through the passage. The pore functions as an electrical resistor wherein the resistance scales as length over cross-sectional area. Changes in the pore cross-sectional area may occur when floppy and somewhat coiled single stranded DNA hybridizes with its complementary strand. Double stranded DNA can be fairly rigid and rod-like. The pore diameter accordingly decreases substantially resulting in a physical blockage of the ion current through the pore. The change in current can be detected.

Solid-state nanopores have proven to be extremely suitable as single molecule sensors, and therefore have significant application to a wide range of fields, including drug discovery. Synthetic nanopores, which are more stable and tunable compared with their biological counterparts, comprise a nanoscale channel or pore (<100 nm) within a thin membrane (e.g. silicon nitride) that separates two aqueous reservoirs containing the electrolyte and analyte(s). By applying an electric potential via electrodes across the membrane, charged molecules are driven ("translocated") through the pore, allowing the nanopore to be used as a single-molecule detector. The detection principle is based on monitoring the ionic current passing through the nanopore as the electric potential is applied across the membrane. When the nanopore is of molecular dimensions, passage of molecules (e.g., proteins or DNA) causes interruptions of the "open" current level, leading to a "translocation event" signal. An electrical fingerprint is created, which can provide information such as size and shape of the molecule. Nanopores can be embedded in a nanofluidic sensor device and used in drug discovery. A schematic representation of a nanopore device containing electrolyte is shown in US 2013/0264219 A1, which is incorporated by reference herein. FIG. 1 shows measurement of open pore current (top) and currents during two translocation events (middle and bottom), with current traces on left and graphical depictions of nanopore and molecules on the right. Target molecules 20 in an electrolyte solution (e.g. KCl) are shown outside a nanopore formed in a membrane 22. A voltage source 24 and an ammeter 26 are electrically connected between electrodes 28, 29 located on opposite sides of the nanopore. In the middle translocation event shown in FIG. 1, a target molecule 20 (or untargeted molecule) passes through the nanopore without binding to a receptor. In the bottom translocation event, the molecule 20 has bound to a receptor 21, producing a current trace that differs from the middle translocation event.

It is often desirable to functionalize the nanopore inner surface with specific molecules. The inner surface of the nanopore may include a functional layer, which is a coating to functionalize the nanopore, (i.e. a coating of the nanopore chosen with a specific purpose in mind). The functional layer can be chosen or configured to interact with predetermined molecules during translocation. Typically, the functionalization layer is attached directly to the nanopore surface as a step in the nanodevice fabrication process. This functionalization of the nanopore permits single molecule sensing. The translocation of a single molecule results in a change of current through the pore. This translocation data can reveal properties of molecules going through the pore on a single molecule level. Indirect measurement techniques, like binding events inside the pore, offer a promising way to determine very specific properties of single molecules. However, incorporating only one single-binding site into a solid-state nanopore is a challenge. There are previous solutions to achieve stochastic sensing with a single-receptor modified solid-state nanopore, including use of a mixed-monolayer assembly on a gold-coated nanopore where the number of receptors inside the pore was controlled by co-adsorption of two different surfactants with different terminal functional groups (one reactive, the other inert).

Graphene is one of several crystalline forms of carbon, alongside diamond, graphite, carbon nanotubes and fullerenes. In this material, carbon atoms are arranged in a regular hexagonal pattern. Graphene can be described as a one-atom thick layer of the layered mineral graphite. High-quality graphene is very strong, light, nearly transparent, and an excellent conductor of heat and electricity. Its interaction with other materials and with light, and its inherently two-dimensional nature, produce properties unique to graphene. Graphene can also be used to create graphene nanopores, that is, nanoscale channels or pores within graphene sheets. This is most commonly done by bombarding a graphene monolayer with a focused ion beam. Nanopores can also be formed in stacks of graphene and solid state membranes. Using the STEM (scanning transmission electron miscroscopy) mode of a TEM, it has recently become possible to preserve the graphene lattice up to the edges of the nanopore and thus preserve the electrical conductivity. Importantly, graphene can be modified with functional groups (molecules chosen with a specific purpose in mind) by both covalent and non-covalent functionalization to interact with predetermined molecules during translocation. For example, graphene can be functionalized by the covalent bond formation between free radicals or dienophiles and C═C bonds of pristine graphene or non-covalently by pi-pi (π-π) stacking. The hydrophobicity of graphene for use as nanopores for DNA translocation can be tailored. Graphene oxide (GO) can be characterized as a single graphitic monolayer with randomly distributed aromatic regions and oxygenated aliphatic regions containing hydroxyl, expoxy, carbonyl and carboxyl functional groups, which can be functionalized using various chemistries known to the art.

SUMMARY

Principles of the invention provide techniques for the detection of translocation events within a nanopore. A method for detecting translocation events associated with a first target molecule while avoiding multiple binding events with respect to the first target molecule is provided. The method includes obtaining an assembly including a first graphene sheet bounded by first and second solid-state membranes and a nanopore extending through the graphene sheet and each of the solid-state membranes, the nanopore having an axis, the graphene sheet being positioned at a selected position with respect to the nanopore axis. One or more receptors selective to the first target molecule are bonded only to the first graphene sheet. An electrolyte solution is introduced to the nanopore. An electric potential is applied across the nanopore and ionic current through the nanopore is detected.

In another aspect, a further exemplary method is provided for the simultaneous measurement of ionic current through a nanopore and multiple tunneling currents. The method includes obtaining an assembly including a plurality of graphene sheets in alternating sequence with a plurality of solid state membranes and a nanopore extending through the graphene sheets and solid state membranes. An electrolyte solution is introduced to the nanopore. An electric potential is applied across the nanopore and ionic current through the nanopore is detected. The method further includes detecting a plurality of tunneling currents within the graphene sheets simultaneously with the step of detecting ionic current through the nanopore.

An exemplary system includes an assembly including a plurality of graphene layers in alternating sequence with a plurality of solid state membranes, one or more nanopores extending through the graphene layers and solid state membranes, a plurality of the graphene layers being electrically connected to one or more detectors configured for detecting tunneling currents associated with charged molecules within the nanopores.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques of the present invention can provide substantial beneficial technical effects. For example, one or more embodiments may provide one or more of the following advantages:

Allows precise control and variability in functionalizing pore surfaces;
Allows control over the position(s) of binding site(s);
Facilitates measurement of single-binding events;
Facilitates avoidance of multiple binding events within a nanopore;
Allows multiple receptor functionalization with only a single binding event;
Enhances binding probability of a single binding event;
Facilitates control of motion of target molecule(s) through a nanopore;
Increases capture rate and hence event rate;
Spatially track the motion of target molecules individually in a plurality of nanopores;
Allows functionalization of different nanopores in a single device for targeting different target molecules;
Facilitates estimation of individual current signals of individual molecules from a combination of a composite ionic signal and a tunneling current signal;
Allows the use of different tunneling current signatures to differentiate between different target molecule types within nanopores, as well as between different conformations or orientations relative to the nanopores of the same molecules.

These and other features and advantages of the present invention will become apparent from the following detailed description of illustrative embodiments thereof, which is to be read in connection with the accompanying drawings.

BRIEF DESCRIPTION OF THE DRAWINGS

FIG. 8 is an exploded, perspective view of a composite nanopore assembly including three layers of solid-state membranes and two layers of graphene strips;

FIG. 9 is an exploded, perspective view of a composite nanopore assembly including three layers of solid-state membranes and four layers of graphene strips;

DETAILED DESCRIPTION

The detection of biological molecules such as proteins, DNA, and enzymes can be useful in the field of diagnostics. The present disclosure provides techniques employing passages such as nanofluidic pores to detect such molecules. Sensing devices capable of using such techniques are further provided for detecting target molecules.

Figure 2:
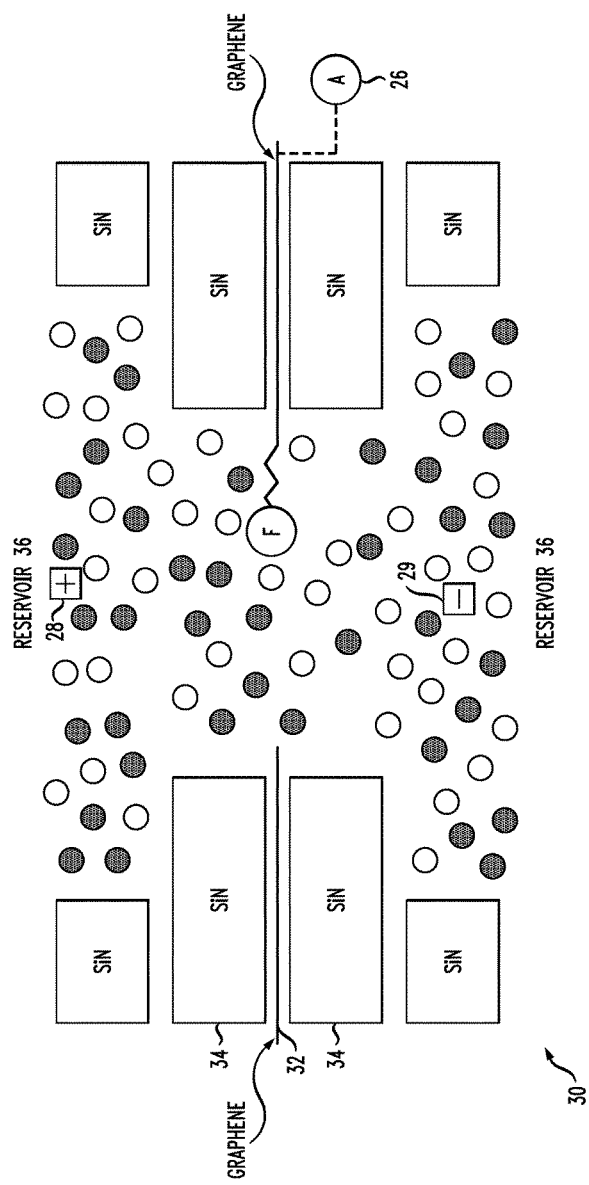
FIG. 2 is a schematic illustration showing an exemplary embodiment of a composite nanopore.
Figure 3:
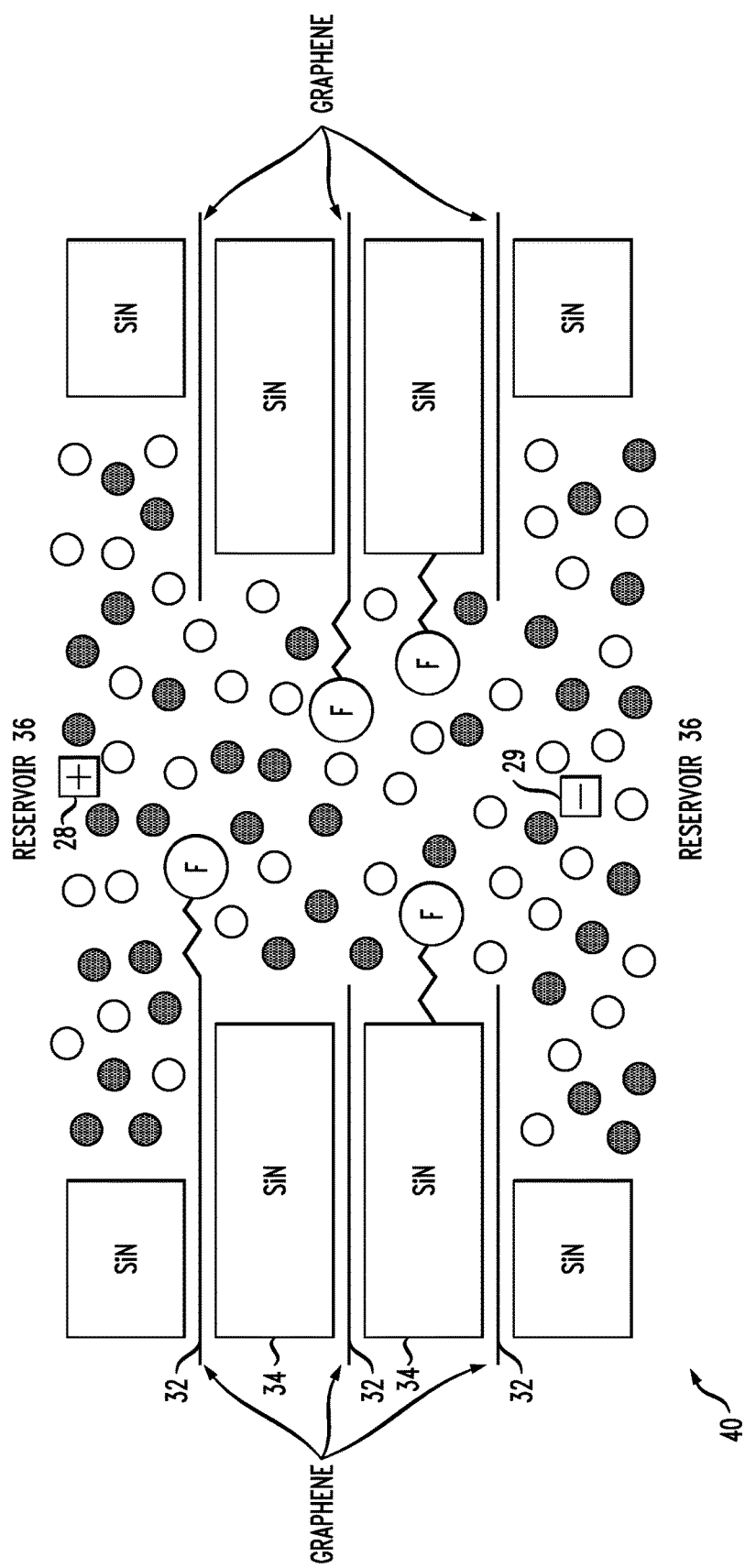
FIG. 3 is a schematic illustration of a second exemplary composite nanopore with functionalized graphene and silicon nitride pore surfaces.

A method for precisely localized functionalization within a nanopore to achieve stochastic sensing with a single-receptor modified solid-state nanopore is provided. The method uses graphene nanopore(s) "sandwiched" between solid-state membranes which are then "sandwiched together" to form a single, composite solid-state membrane such as shown in FIGS. 2 and 3. This composite membrane forms the substrate for the subsequent functionalization of the nanopore, which is accomplished by functionalizing the edge of the graphene nanopore inside the solid-state nanopore, as shown in FIG. 2. In another embodiment, multiple graphene nanopores are sandwiched between many layers of solid-state nanopores, yielding multiple graphene nanopore edges for functionalization. The surface of the solid-state nanopore is itself functionalized in some embodiments. The nanopores can be formed in the graphene sheets and individual membranes before they are layered with the pores aligned; in this case, the graphene nanopores and solid-state (e.g. $Si_xN_y$, SiO, etc) nanopores may be of different sizes, as depicted in FIG. 3. In this approach, the graphene can be functionalized before or after fabrication of the composite nanopore. Alternatively, the graphene and solid-state membranes can be sandwiched together first, then the nanopore fabricated (drilled) in the composite membrane, followed by functionalization. Functionalization is done after nanopore fabrication, by bonding (covalently or otherwise) the functionalization molecules to the graphene and, optionally, the solid-state ($Si_xN_y$, SiO, etc) membrane. The composite nanopore can be constructed with just the graphene edge(s) exposed inside the nanopore, or with part of the graphene sheet protruding into the nanopore, exposing a portion of the surface of the graphene sheet. When just the edges are exposed, functionalization is limited to just the edges, but when parts of the graphene top and bottom surfaces are exposed, the top and bottom surfaces are then available for functionalization via pi-pi stacking When functionalizing the edge, the graphene edges can first be oxidized, creating functionalization sites which can then be functionalized with specific functionalization molecules (e.g. receptors, ligands, etc).

Referring to FIG. 2, an exemplary nanopore structure 30 includes a single graphene layer 32 having a nanopore that is functionalized with a receptor F. the graphene layer is positioned between $Si_xN_y$ (e.g. $Si_3N_4$) membranes 34. The nanopores formed within the membranes 34 are larger than that formed in the graphene layer 32 in this exemplary embodiment. The nanopores are bounded by reservoirs 36 containing electrolyte solution. As discussed above, electrodes 28, 29 are provided within the reservoirs on each side of the composite membrane formed by the solid-state membranes 34 and the graphene layer 32, enabling translocation through the nanopores.

FIG. 3 shows a composite nanopore structure 40 having three graphene nanopores layered between solid-state, dielectric membranes 34 containing nanopores. (The same reference numerals employed in FIG. 2 are used to designate similar elements.) In this embodiment, two of the graphene layers 32 are functionalized as well as one of the solid-state membranes 34. The receptor molecules F may or may not be the same. It will be noted that there are a plurality of locations for functionalization in this embodiment at specific locations within the nanopore formed by the composite membrane.

Figure 4:
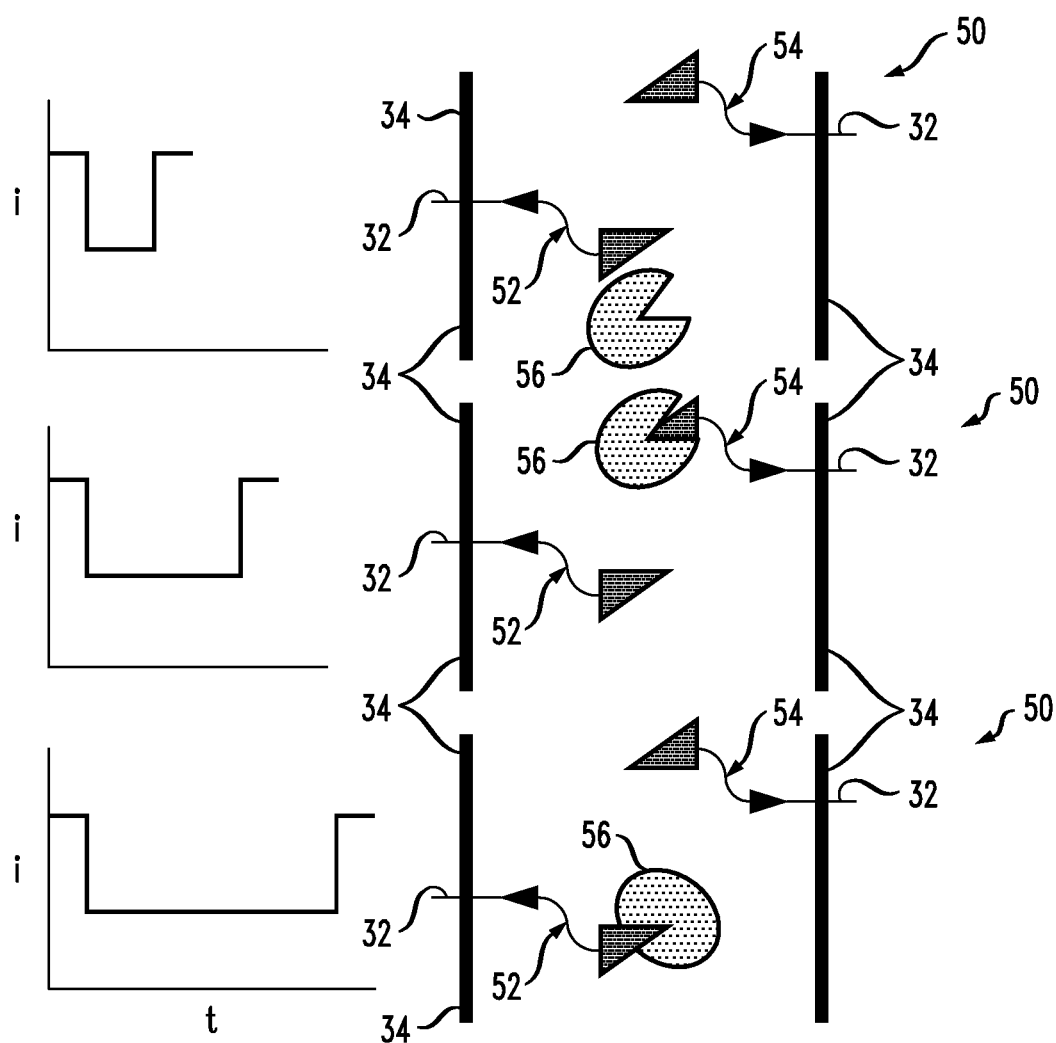
FIG. 4 is a schematic illustration showing a composite nanopore functionalized with two different receptors at different locations and current traces of translocation events therein.

A composite nanopore device 50 functionalized with two different receptors 52, 54 at precisely controlled locations determined by the positions of the graphene layers 32 is shown schematically in FIG. 4. In this exemplary device, graphene layers 32 define a plurality of nanopores. The binding sites are at known positions within the nanopore defined by the composite membrane formed by the graphene layers 32 and adjoining solid-state membranes 34. Different current traces are accordingly obtained depending on the factors such as the presence or absence of a target molecule (or other large molecule) within the nanopore, the binding of a target molecule to a first type of receptor, or the binding of a target molecule to a second type of receptor. As shown in the top portion of FIG. 4, a target molecule has passed through the device 50 without binding to any of the receptors 52, 54 therein. Such a translocation event results in the current trace shown at the top left obtained using a detection system as described above with respect to FIG. 1. A different current trace is obtained when a molecule 56 binds with a receptor 54, as shown in the middle translocation event depicted in FIG. 4. A third type of current trace is obtained by the bottom translocation event shown in FIG. 4 wherein a molecule 56 binds with the receptor 52.

In one or more embodiments, a voltage is applied to selected graphene layers to facilitate binding events. The graphene layers can accordingly function as graphene nanopore electrodes that are used to control the motions of molecule(s) within the nanopore at desired (functionalized) regions. This technique, explained further below, increases the probability of binding of a target molecule and allows a longer time study of the interaction of the molecule with a target receptor.

Composite nanopore devices including only a single receptor, such as shown in FIG. 2, facilitate precise detection of single molecules. Such devices avoid multiple uncontrollable receptors along the nanopore axis and thereby avoid subsequent multiple binding events. The resulting electrical current from such devices is simple and straightforward to analyze, and offers a method to study the association and disassociation kinetics of the target bio-molecule with the receptor. The opportunity of having only two different translocation scenarios, one where a molecule binds to the binding site inside the nanopore versus one other where no such binding took place, allows reliable and rapid interpretation of the translocation data. In contrast, the interpretation of translocation data of prior art devices can be very time consuming, complicated and uncertain due to the possibility of having several binding sites within the nanopore leading to multiple binding events.

In one or more embodiments, a composite nanopore structure is functionalized on the circumference of a chosen location, namely the graphene nanopore, along the nanopore axis. Such a structure, while including multiple receptor functionalization, permits only a single binding event. If the graphene nanopore includes only a single binding site, the binding of a biomolecule to the receptor can be missed due to the variability in the orientation of both the receptor and the target molecule. By functionalizing the nanopore with multiple receptors along the circumference of a specific location, the probability of binding is enhanced by avoiding the problems arising from orientation while allowing only a single binding event. The inner surface of the nanopore may include a functional layer, which is a coating to functionalize the nanopore, (i.e. a coating of the nanopore chosen with a specific purpose in mind) and the functional layer can be chosen or configured to interact with predetermined ones of the molecules during translocation. Typically, the functionalization layer is attached directly to the nanopore surface as a step in the nanodevice fabrication process. This is accomplished by filling the reservoirs with the functionalization molecules in an appropriate solvent (e.g. water). Functionalization molecules typically consist of three components: a binding group bound to a linker which in turn is bound to a functional group. When the functionalizing molecules diffuse into the nanopore during pore wetting, the binding groups covalently bond the functionalization molecules to the nanopore surface through a directed self-assembly process. Linkers and functional groups then extend into the pore towards its center and form the functional layer. In operation, after unbinding from a receptor, a targeted molecule will simply pass through the nanopore rather than binding to another receptor. The use of multiple receptors in this manner increases binding probability without causing more than a single binding event.

It will be appreciated that the devices described above and the manner in which they are fabricated facilitate the precise positioning of binding sites within a nanopore. The available binding sites adjoining a graphene nanopore are very limited. Graphene sheets including nanopores positioned within a composite solid state structure as described provide isolated binding sites at locations that are controlled by depositing electrically insulating layers of selected thickness between graphene layer(s). Having complete knowledge of the exact location(s) of binding sites within a nanopore facilitates effective molecule detection and study.

Graphene, which has excellent electron transport properties, can further function as a molecular detector via tunneling current. As a charged molecule passes through a graphene nanopore, the charge on the molecule attracts or repels nearby electrons in the graphene sheet, leading to a global rearrangement or movement of electrons within the entire graphene sheet. The tunneling current allows the graphene nanopore to be treated as an electrode measuring the passage of charged molecules through the graphene nanopore. Moreover, when multiple molecule types (e.g. multiple proteins and/or ligands) translocate through the graphene nanopore, they will typically exhibit different tunneling currents. Similarly, the same molecule (e.g. protein) will exhibit different tunneling currents based upon, for example, their conformation or their orientation relative to the nanopore.

Figure 5:
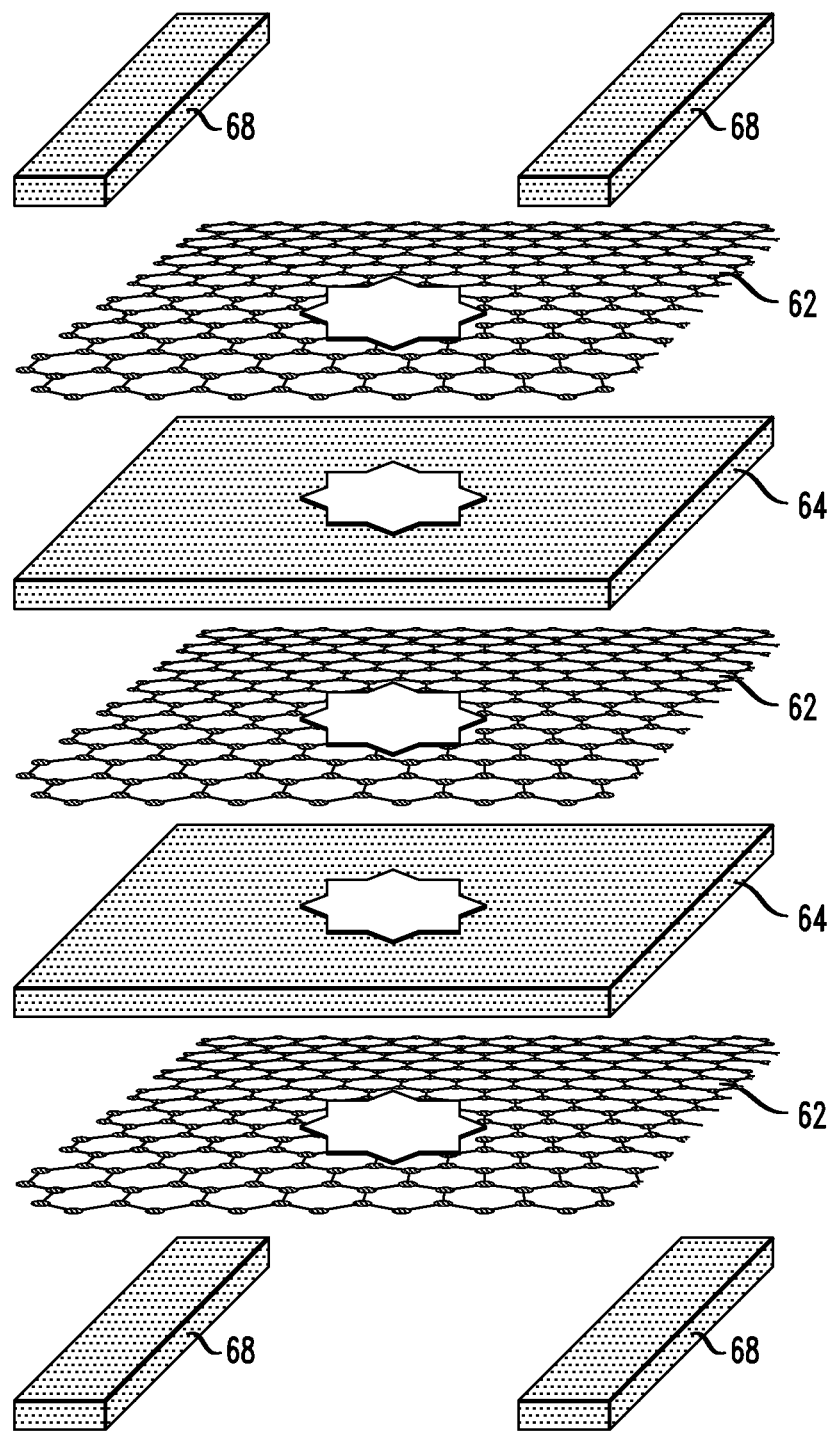
FIG. 5 is an exploded, perspective view of alternating graphene sheets and solid-state membranes.
Figure 6:
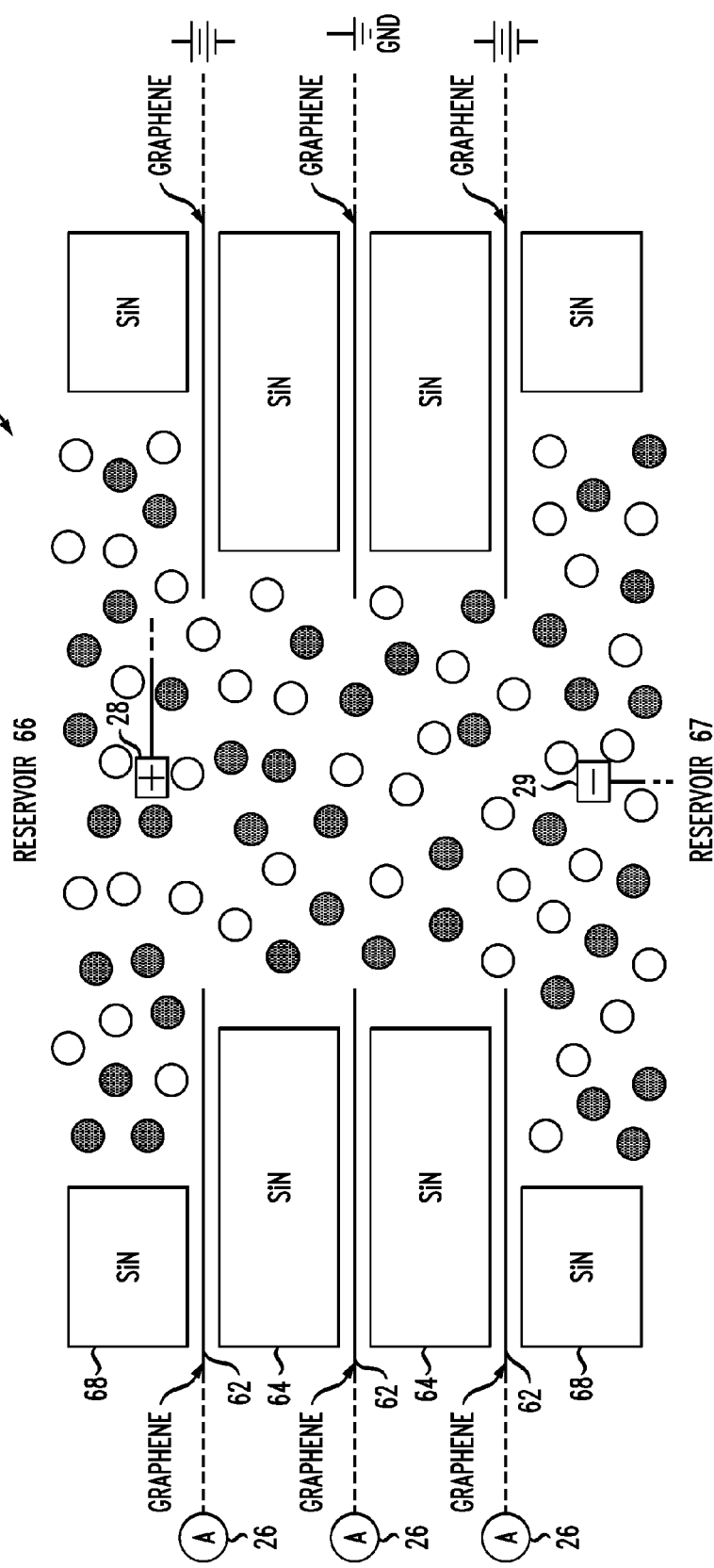
FIG. 6 is a schematic illustration of a composite nanopore formed from the alternating graphene sheets and solid-state membranes shown in FIG. 6A.

Referring now to FIGS. 5 and 6, nanopores are formed in stacks of graphene and solid state membranes. As shown in FIG. 5, an exemplary composite nanopore structure is formed from alternating graphene sheets 62 and solid-state membranes 64 that are stacked together. In an exemplary method, nanopores are formed in both the graphene sheets and solid-state membranes prior to assembly and are aligned during assembly. FIG. 6 schematically illustrates the resulting composite nanopore structure 60 with associated reservoirs 66, 67, support blocks 68 and electrolyte solution. The use of receptors in association with the graphene sheets is optional in this embodiment as the graphene sheets 62 can be used as electrode sensors. Ammeters 26 are electrically connected to the graphene sheets 62 to detect changes in tunneling current within the graphene portions of the composite nanopore. Electrodes 28, 29 are then inserted into the reservoirs 66, 67 on either side of the composite nanopore to establish the electric potential across the composite membrane that causes the charged target molecules to move through the nanopore. The ionic current through the nanopore is measured using appropriate instrument(s) electrically connected to the electrodes. In some embodiments, metal electrodes are electrically connected to the graphene sheets to facilitate connection to detection device(s) for detect tunneling currents as the charged target molecules move through specific locations within the interior of the nanopore. Voltage sources are optionally electrically connected to the graphene layers to enable the trapping of charged molecules.

A multi-electrode solid-state nanopore analysis method is possible using one or more of the disclosed devices that permits the simultaneous measurement of the ionic current through the nanopore and multiple tunneling currents indicating the progress of multiple molecules passing through the nanopore simultaneously. As shown in FIGS. 5 and 6, an exemplary device 60 includes N graphene sheets deposited onto N−1 solid-state membranes which are then stacked to form a single, composite solid-state membrane. This composite membrane forms the substrate for the subsequent fabrication of a nanopore in some embodiments, resulting in a nanopore with N layers of graphene-nanopore electrodes. In other embodiments, the nanopores are formed in the graphene sheets and membranes prior to assembly.

Figure 7A:
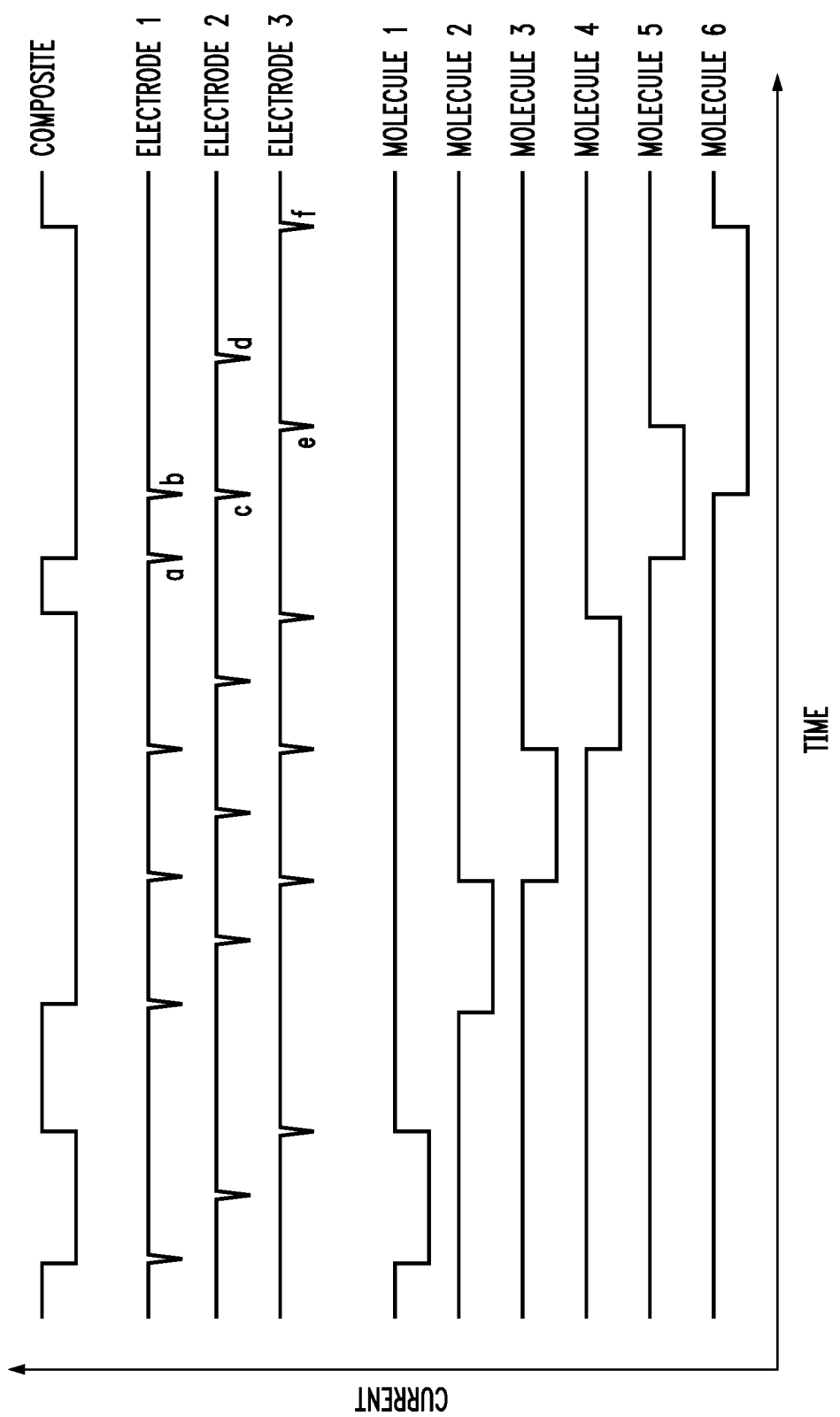
FIG. 7A is a graph showing idealized current traces versus time of six molecules translocating the nanopore of a three-electrode exemplar of a multi-electrode nanofluidic sensor device.

As molecules pass through this multi-electrode nanosensor, the composite ionic current signal measures the total number of molecules in the nanopore—or at least the presence of molecules in the nanopore—and the graphene electrodes track spatially the progress of the individual molecules within the nanopore, as illustrated in FIG. 7. FIG. 7 shows idealized current traces versus time of six target molecules translocating the nanopore of a three-electrode (three graphene electrodes comprising the graphene sheets 62) exemplar of the multi-electrode nanofluidic sensor device, including composite current through the nanopore (Composite) using the electrodes positioned in the reservoir areas just outside the nanopore, three tunnelling currents from the graphene electrodes (Electrode 1 through 3) and six computed ionic currents due to the six molecules. Six tunneling current events are identified (a-f). When the concentration of analytes or the thickness of the pore is large, or the pore diameter is wide, the pore can be occupied with multiple molecules at the same time, or simultaneous entry/exit of the target molecules can occur, leading to a very complex ionic current signature. The ionic current through the pore is not proportional to the number of molecules inside the nanopore. Hence, identifying such events to discern the individual translocation events from the composite signal is not possible using the conventional nanopore ionic currents. The method disclosed herein using the multi-electrode nanofluidic device can accurately calculate the entry/exit, number of molecules inside the pore and their positions and velocities inside the nanopore by analyzing the composite ionic current and tunneling currents at various electrodes.

Figure 7B:
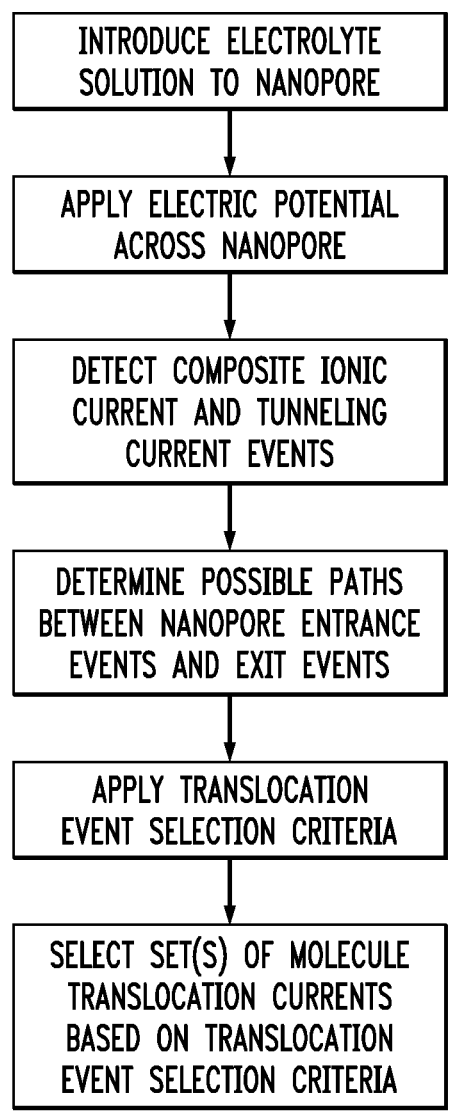
FIG. 7B is a flowchart showing exemplary steps for selecting set(s) of molecule translocation currents.

A method for estimating the individual current signals of the individual molecules from a combination of the composite ionic signal and the tunneling current signals is provided herein. When the composite ionic current through the nanopore, as detected by the electrodes in the reservoirs on opposite sides of the nanopore, is reduced due to the presence of molecules in the nanopore, tunneling currents from the graphene electrodes are monitored and analyzed to track entrance into, movement through and exit from the nanopore; the tunneling current events correspond to the "blips" seen in the electrode current traces in FIG. 7A. The composite ionic current groups the tunneling current events, which are then analyzed in groups to determine molecular translocation currents consistent with both the composite ionic current and tunneling current events. To that end, within each group, all possible paths are drawn between all entrance events and exit events passing through translocation events subject to the constraints that no path may correspond to a molecule moving backward in time, and all events must occur in one and only one path. A single set of molecule translocation currents is then chosen based upon some measure of goodness, for example, that set of molecular translocation currents which correspond to the least variability in molecule speed while traversing the nanopore, or the least variability in magnitude and shape of the tunneling currents. For example, in one embodiment we must find two translocation paths through the tunneling current events (a-f) in the third group in FIG. 7A, entering at a and b, going through c and d, and exiting at e and f. Two possibilities (a-d-e and b-d-e) can be eliminated by the constraint that a molecule cannot move backward in time, implying that one path must go through c and e, and the other must go through d and f. This leaves two possible combinations: a-c-e and b-d-f, or a-d-f and b-c-e. The paths a-c-e and b-d-f correspond to paths of constant speed (though their constant speeds are different), whereas the paths a-d-f and b-c-e have considerable variability in their speed as they translocate through the nanopore. Hence, we choose a-c-e and b-d-f in this exemplary embodiment. The flowchart provided in FIG. 7B shows exemplary steps in obtaining and processing the data shown in FIG. 7A.

Some embodiments of the method further include the use of different tunneling current signatures to differentiate between different molecule types within the nanopore, as well as between different conformations or orientations relative to the nanopore of the same molecule. Tunneling currents have characteristic forms pointing to specific biomolecules. This sensing technology is known in the art as "recognition tunneling". The use of functionalized electrodes to interrogate single molecules has been described in the art.

When biomolecules such as proteins go through nanopores, conformational changes (e.g. as a result of their interaction with another compound or ligand) or orientations can occur. If these changes are small, they cannot be detected using conventional SiN nanopore ionic currents. Such conformational changes can have a profound effect on their binding sites and their interaction with the ligands (possible drugs). Hence identifying such conformational changes can be very important and a major challenge in biosensing applications. The multi-electrode device and method disclosed herein can detect such conformational changes in the proteins/molecules inside the nanopore. As the protein molecules pass through the pore, the graphene nanopore electrodes along the pore are used to measure the tunneling currents modulated by the protein. As these currents are very sensitive, they can detect any conformational changes in the molecules inside the nanopore. These changes in tunneling currents are reflected in the magnitude and shape of the tunneling currents within the electrodes. Recently it has been found that the conventional SiN nanopore ionic currents are inefficient in detecting small protein molecules, due to their limited sensitivity. Graphene nanopores (electrodes) can detect such small molecules as the tunneling currents are very sensitive. The multi-electrode device and corresponding analysis method accordingly allows the simultaneous detection of small proteins within the nanopore.

As the electric field inside the nanopore varies along the pore axis, a molecule passing through the pore can have different velocities at different positions along the pore. Understanding the protein motion/velocity inside the pore is also very important in some biosensing applications. By monitoring the tunneling currents at various locations inside the nanopore as a function of time, and computing the trajectories of individual molecules within the nanopore, calculation of the molecular velocities at different locations along the pore is also performed in one or more embodiments. As discussed above, the graphene electrodes are further employed for controlling the position of the molecules within the nanopore, similar to the use of metal electrodes in U.S. Pat. No. 8,003,319, which is incorporated by reference herein. Controlling the motion of the molecule inside the nanopore is very important in studying its interaction with other molecules inside the pore in some embodiments. Nanopores without any functionalization on the nanopore surface offer a limited control over the molecule motion inside the pore. By controlling the electric fields produced by applying an electric potential to the graphene, the molecules' progress through the nanopore can also be controlled, such as slowing down/speeding up or even trapping the molecule in a desired region along the pore. Trapping the molecule in a specific region has the additional advantage of allowing the molecule to interact with the other molecules inside the nanopore, and longer time observation. As shown in FIG. 6, two of the graphene sheets 62 are optionally connected to voltage sources while the middle graphene sheet is connected to ground. The middle graphene layer may or may not be functionalized. In operation, a well is created that traps charged molecules (such as protein molecules) between the upper and lower graphene sheets 62.

One of the main hurdles in protein characterization using nanopores is the low event rate within a given time. Typically a single nanopore is drilled in a membrane and the molecules are characterized by an ionic current as they pass through the pore, such as described above with respect to FIG. 1. Because there is only one nanopore, molecule translocation is a fairly rare event. One way to overcome this low rate is to utilize multiple pores in the membrane. For example, the nine nanopores shown below in FIGS. 8-10 can increase the translocation rate by a factor of approximately nine. In the absence of the graphene sheets, the devices/methods would have a significant disadvantage in that they would measure only the total ionic current through the pores, making it very difficult (if not impossible) to count the number of molecules inside or translocating the pore and their characterization. As the molecules enter, translocate and leave different pores simultaneously, the signature of the total ionic current is continuous rather than step-like enough to detect the events and characterize the molecules.

The graphene-based systems and methods for detection of single molecule translocation events in muti-pore nanopore arrays as shown and described below facilitate processes such as protein characterization. As shown in FIG. 8, an exemplary device 80 comprises alternating layers of solid-state membranes 84 and elongate graphene strips 82, each containing multiple nanopores 85, 83 that, when the membranes 84 and strips 82 are stacked on top of each other, are substantially coaxial and form composite nanopores that pass through alternating layers of solid-state membranes and graphene strips. The discrete graphene strips comprising each graphene layer are rectangular and parallel in some embodiments. The graphene strips in adjoining layers alternate in direction, running perpendicular to the strips in the graphene layer(s) above and/or below. Each graphene strip accordingly overlies a plurality of graphene strips in an adjoining graphene layer. The graphene layers are electrically isolated by the dielectric, solid-state membranes 84. FIG. 8 shows one embodiment, a configuration containing two layers (one pair of two layers) of graphene strips. FIG. 9 shows another exemplary device 90, with multiple pairs of graphene layers. The devices 80, 90 as assembled comprise composite nanopore arrays; the alternating layers of membranes and graphene comprise composite membranes; the nanopores 85, 83 comprise composite nanopores. The arrangement of graphene strips 82 facilitates the formation and accessibility of metal electrodes (not shown) or wiring that are electrically connected to the strips 82. The entire circumference of the device is available to form the necessary electrodes. In contrast, if the strips comprising each graphene layer all ran in the same directions, electrical connections would only be possible at two ends.

Figure 10:
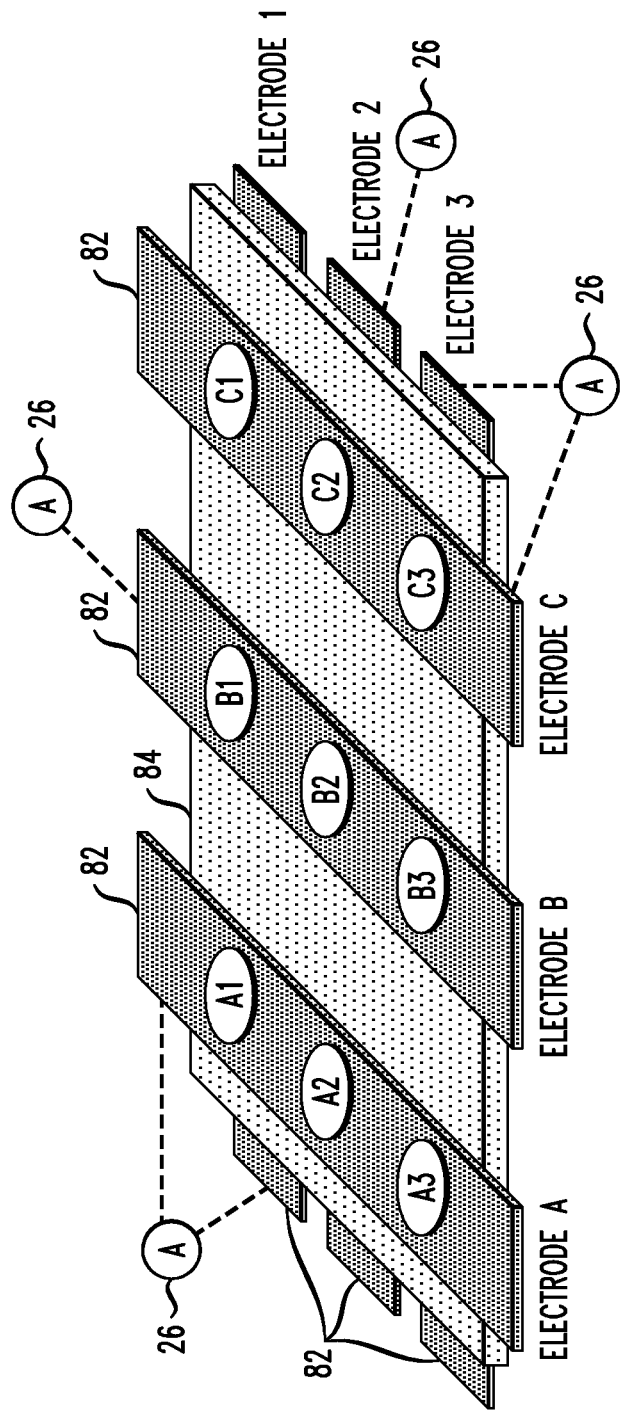
FIG. 10 is a schematic illustration showing a composite nanopore array with each electrode and each composite nanopore labelled.

Each graphene strip 82 acts as an electrode capable of detecting the translocation of charged molecules through any of the nanopores passing through the strip. Because the graphene strips alternate in direction from layer to layer, a charged molecule translocating the entire length of the composite nanopore will be detected by strips alternating in direction. FIG. 10 shows the composite nanopore array corresponding to FIG. 8 with each electrode (graphene layer) and each composite nanopore labelled for explanatory purposes. In this exemplary figure, any charged molecule translocating from top to bottom through, for example, the nanopore labelled A2 will first be detected by electrode A, and then by electrode 2. Another charged molecule translocating from top to bottom through, for example, the nanopore labelled C3 will first be detected by electrode C, and then by electrode 3.

Electrodes are then inserted into the reservoirs on either side of the device 80, 90 to establish the electric potential across the composite membrane that causes the charged molecules through the nanopores of the device. Each reservoir communicates with all nine composite nanopores of the exemplary composite nanopore devices 80, 90 shown in FIGS. 8 and 9. The reservoir electrodes and associated detector measure the ionic current through the combination of nanopores. Additional (e.g. metal) electrodes are attached to the graphene strips to facilitate connection of the graphene strips to detector(s) 26 that detect tunneling currents as the charged molecules move through the interiors of the composite nanopores. (While multiple detectors 26 are shown, it will be appreciated that a single detector may, in some embodiments, be employed to receive multiplexed data from a plurality of graphene strips.) As molecules pass through this multi-electrode nanosensor device 80 or 90, the composite ionic current signal measures the total number of molecules in the composite nanopores, and the graphene electrodes track spatially the progress of the individual molecules within each composite nanopore. The combination of these signals enables detection of the number of molecules passing through the array of composite nanopores. The thickness of the solid state membranes 84 can be adjusted during device fabrication in order to retain the size and shape characterization ability of these composite nanopore devices. For example, specific applications may require a nanopore that is at least fifty nanometers in length to provide sufficient translocation time and include at least three layers of graphene. The thickness of the solid state membranes can be selected so that the desired nanopore length and graphene layer spacing is achieved. In one or more embodiments, the graphene sheets are separated from each other by five to ten nanometers.

Figure 11:
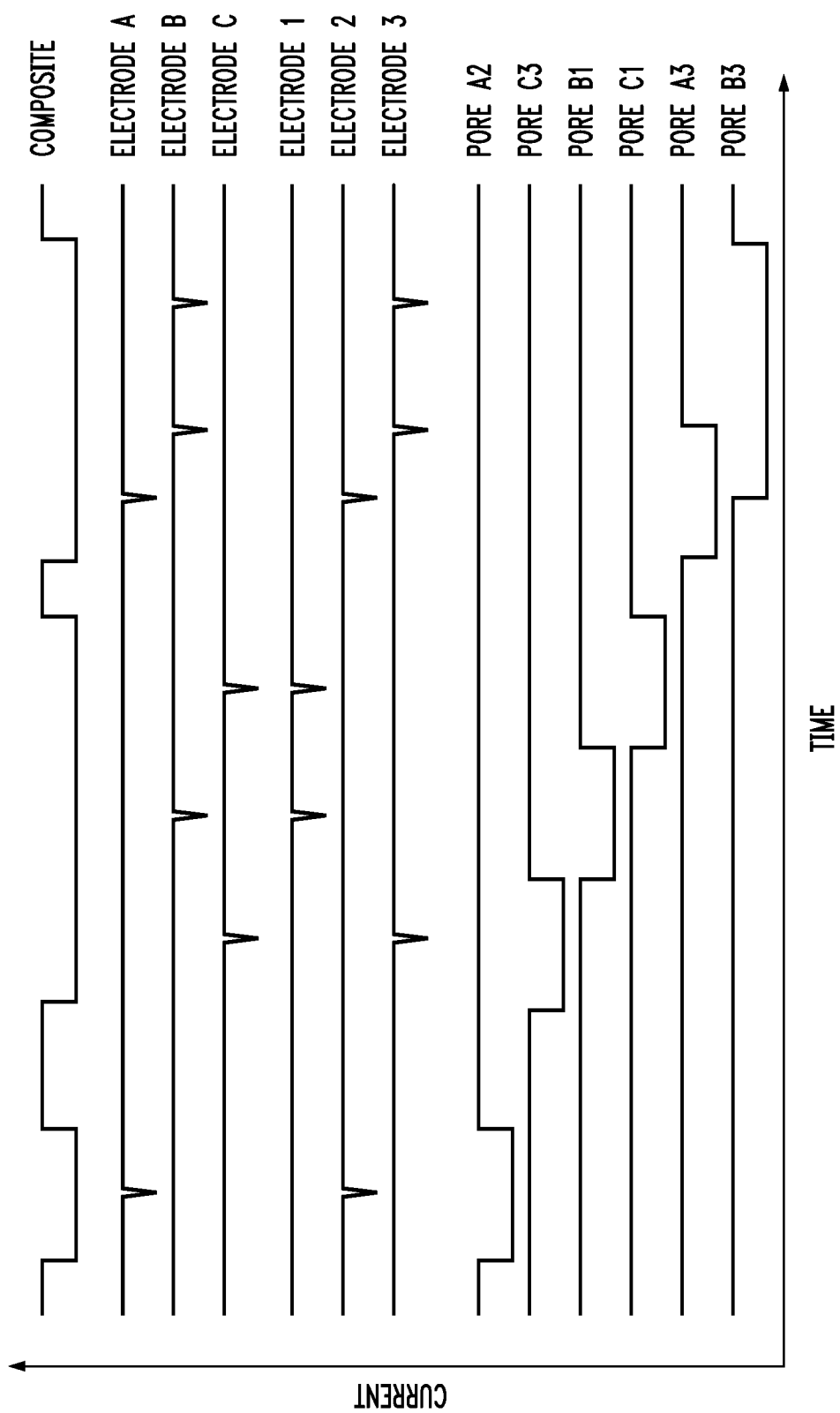
FIG. 11 is a graph showing current traces corresponding to translocation events within the composite nanopore array shown in FIG. 10.

FIG. 11 shows idealized current traces for molecules passing through the assembly shown in FIG. 10, with reference to the labelled electrodes and nanopores. The "composite" trace represents the ionic current detected by the electrodes in reservoirs adjoining the top and bottom surfaces of the assembly. The tunneling current events are indicated by the traces designated by the electrodes comprising the graphene layers. Computed ionic currents corresponding to six molecules detected by the sensor are identified with respect to individual nanopores.

The graphene-based multi-electrode and multi-pore composite devices disclosed herein with reference to FIGS. 8-11 facilitate single molecule detection and characterization. Each device contains N pores, which increases the capture rate and hence event rate by roughly N times over the conventional single nanopore membranes. Along with detecting the entry and exit of the molecules, the device spatially tracks the motion of molecules individually in each pore. Hence the device can offer several paradigms of molecular detection and characterization with multiple pores at the same time. Altering the thickness of the solid state nanopore within the composite nanopore can increase the versatility of the device in characterizing molecules that pass through the multiple layers of the devices structure. In one or more embodiments, the step of identifying the nanopore occupied by a molecule in a multi-pore composite membrane is performed. The multipore device can further be used to study the interaction of a target molecule with different receptors in a single experiment by functionalizing the nanopores differently. The use of different receptors further enables the characterization of test molecules simultaneously in a single device. The tunneling currents facilitate identifying each pore that is occupied by a molecule.

There are many ways to fabricate graphene to form the graphene sheets or strips as discussed above with reference to the exemplary embodiments, including: 1) Mechanical exfoliation, where graphene flakes are individually extracted using adhesive tape; this process is not scalable, so it is considered impractical for commercial manufacturing purposes; 2) Liquid-phase exfoliation involves suspending carbon-carrying materials (such as graphite) in a liquid with high surface tension, then bombarding the suspension with sound to extract graphene flakes; 3) Chemical vapor deposition (CVD) condenses a volatile substance containing carbon onto a copper surface. The graphene layer that forms can then be peeled off onto another substrate; 4) Growing graphene directly onto a silicon carbide wafer by selectively extracting the silicon atoms in the top layer via sublimation (vaporizing a solid). The solid-state dielectric membranes which separate neighboring graphene sheets in the exemplary structures can optionally also be composed of multiple layers themselves. Formation of such multilayer membranes might be necessary due to applicable membrane and graphene fabrication techniques as described in more detail below.

The graphene fabrication process chosen may depend on the dielectric layers selected for the solid-state membranes of the composite structure. Extremely high temperatures (i.e. exceeding 600° C.) are required to form some dielectric layers. Such high temperatures may destroy previously deposited graphene sheets in the stack and therefore should be avoided when forming multiple insulating dielectric layers. For example, a first graphene electrode (sheet or strip) may be deposited onto a first membrane substrate using a first graphene fabrication technique. The temperature required to form the first membrane substrate is accordingly immaterial as it is formed prior to graphene deposition. A second dielectric membrane layer is then deposited onto the first graphene electrode using a low temperature deposition method, limiting the material choices for that second dielectric layer. Depending on the type of material for forming the second dielectric layer, a second graphene electrode is then deposited onto the second membrane using a second graphene fabrication technique and so forth. The following multi-membrane fabrication scheme depicts an exemplary fabrication flow for a multi-membrane stack incorporating two different graphene fabrication techniques and a low temperature dielectric layer deposition technique: 1) Graphene sheet 1 is deposited onto a SiN membrane using chemical vapor deposition (CVD); 2) An aluminum oxide or zirconium oxide dielectric layer is deposited onto Graphene sheet 1 using low atomic layer deposition (ALD); 3) Graphene sheet 2 is deposited onto the dielectric layer using mechanical exfoliation. Alternatively, the membrane fabrication process might require composing a membrane layer to consist of two or more sublayers. This might be necessary if the dielectric deposition method of choice is not directly compatible with graphene surfaces or vice versa if a graphene deposition method of choice is not directly compatible with a dielectric layer surface or both. In such cases an intermediate dielectric layer is deposited onto the graphene layer before the bulk dielectric is deposited or onto the bulk dielectric layer before the subsequent graphene layer is deposited. In such cases one single membrane layer may consist of a bulk dielectric layer and at least one intermediate dielectric layer. Metal electrodes are deposited on the graphene sheets using conventional technology; the choice of deposition techniques should take the temperature limitations discussed above into consideration. Various methods are known for fabricating nanopores up to at least one hundred nanometer diameters in graphene and dielectric materials, including TEM and He-Ion microscopes.

In order to achieve device functionality, nanopore locations in the dielectric layers need to be aligned with the locations of the respective graphene sheets or strips in the stack. Every sub-layer of graphene sheets comprises a specific lateral in-plane pattern that needs to be aligned with all other graphene sheet patterns in other layers of the composite membrane. In other words, lithographic patterning of the graphene sheets may be necessary so that the various sheets have selected overlap with other graphene sheets above or below. In some embodiments, a specific graphene sheet may be supposed to overlap with the neighboring layer above but not with the neighboring graphene sheet below. Solid state membranes themselves show no in-plane pattern and thus do not need to be aligned with other device features or components. In one exemplary embodiment, the location of each graphene sheet in a specific graphene layer is defined and registered by means of at least one alignment mark which is generated in this graphene sheet layer together with the individual graphene sheets. Deposition of the subsequent solid state membrane happens in such a way that the alignment mark from the graphene sheet is carried over and also re-created in the deposited solid-state membrane layer. Another subsequent set of graphene sheets is then deposited onto this solid state membrane in an aligned way with respect to the alignment mark. The process is followed for all subsequent solid state membranes and graphene sheet layers to form the full composite membrane. Nanopores are then drilled through the full composite membrane using the alignment marks on the top solid state membrane or graphene sheet layer, depending on what the last cover layer to be deposited was chosen to be.

Figure 1:
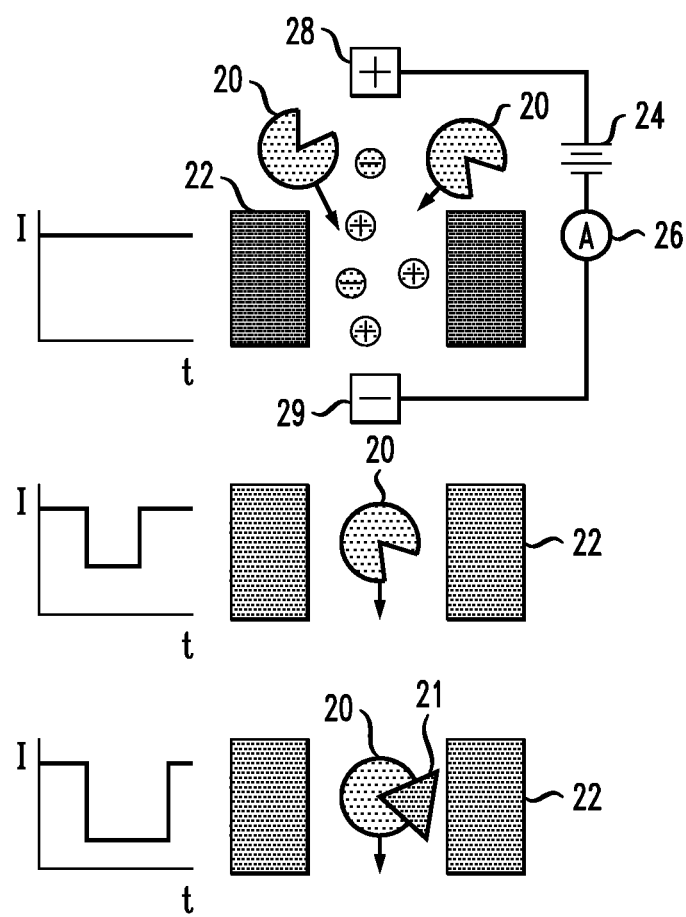
FIG. 1 is a schematic illustration of a prior art biomolecule sensing device and current traces of two translocation events.

Given the discussion thus far, and with reference to the drawings and accompanying disclosure, an exemplary method for detecting translocation events associated with a first target molecule while avoiding multiple binding events with respect to the first target molecule is provided in accordance with one or more embodiments. The method includes obtaining an assembly (e.g. structure 30 as shown in FIG. 2 or structure 40 as shown in FIG. 3) including a first graphene sheet 32 bounded by first and second solid-state membranes 34 and a nanopore extending through the graphene sheet and each of the solid-state membranes, the nanopore having an axis, the graphene sheet being positioned at a selected position with respect to the nanopore axis. One or more receptors (e.g. receptor F) selective to the first target molecule is bonded only to the first graphene sheet. Such an arrangement is shown in FIG. 2. If the embodiment of FIG. 3 is employed, where multiple receptors F are employed at different locations along the nanopore axis, only one of the illustrated receptors is selective to the first target molecule. An electrolyte solution is introduced to the nanopore. An electric potential is applied across the nanopore. Electrodes 28, 29 such as schematically illustrated in FIG. 2 are employed for applying an electric potential across the nanopore. Ionic current through the nanopore is detected using, for example, an ammeter 26 as illustrated in FIG. 1 in one of the exemplary structures 30, 40. The method, in which either a targeted molecule binds at a specific location within the nanopore or no binding takes place, allows reliable and rapid interpretation of the data obtained. After unbinding from the receptor, the target molecule will simply pass through the remainder of the nanopore with no further binding events. In some embodiments, the method further including the step of detecting a tunneling current within the first graphene sheet, using the graphene sheet as a detection electrode. A plurality of receptors is bonded to the graphene sheet in some embodiments. As discussed above, by functionalizing the inner circumference of the graphene sheet to accommodate multiple receptors, all selective to the target molecule, the graphene portion of the nanopore still only permits a single binding event within the nanopore while enhancing binding probability of a target molecule. In some embodiments, only an edge of the graphene sheet is exposed to the nanopore. The method may then further include the step of oxidizing the edge of the graphene sheet prior to bonding the one or more receptors. In some embodiments, the graphene sheet includes a portion protruding into the nanopore, as shown in FIGS. 2 and 3, in which case the exposed graphene surface can be functionalized via π-π stacking.

An exemplary method for the simultaneous measurement of ionic current through a nanopore and multiple tunneling currents is further provided. The method includes the use of an assembly including a plurality of graphene sheets in alternating sequence with a plurality of solid state membranes and a nanopore extending through the graphene sheets and solid state membranes. An exemplary assembly including such graphene sheets 62 and solid state membranes 64 is shown in FIG. 6. An electrolyte solution is introduced to the nanopore and an electric potential is applied across the nanopore. Ionic current through the fluidic passage defined by the nanopore is detected as the electric potential is applied using, for example, electrodes 28, 29 positioned in reservoirs at either end of the nanopore. In addition, the method includes detecting a plurality of tunneling currents within the graphene sheets 62 simultaneously with the step of detecting ionic current through the fluidic passage. The method may further include the step of estimating individual current signals of individual molecules from a combination of the detected ionic conductance through the nanopore and the detected plurality of tunneling currents. Such estimation may include obtaining tunneling current events from the detected plurality of tunneling currents and analyzing the tunneling current events to obtain molecule translocation currents consistent with both the detected ionic conductance through the fluidic passage and the tunneling current events. Exemplary estimation techniques are discussed above with reference to FIGS. 6 and 7. For example, estimation may be facilitated by selecting a single set of molecule translocation currents based on least variability of at least one criterion such as molecule speed through the nanopore, magnitude of the tunneling currents, or shape of the tunneling currents. Some embodiments of the method further include the step of determining molecular velocity within the nanopore by monitoring the tunneling currents as a function of time.

An exemplary system includes an assembly including a plurality of graphene layers in alternating sequence with a plurality of solid state membranes. One or more nanopores extend through the graphene layers and solid state membranes. The exemplary structure shown in FIG. 5 shows one nanopore that extends through a plurality of graphene layers 62 and a plurality of solid state membranes 64 while the exemplary structures 80, 90 shown in FIGS. 8 and 9 include a plurality of nanopores 83, 85 extending through graphene strips 82 and solid state membranes 84, respectively. A plurality of the graphene layers are electrically connected to one or more detectors 26 configured for detecting tunneling currents within the graphene layers 62 associated with charged molecules at specific locations within the nanopores. Some embodiments of the system further include a plurality of nanopores extending through the graphene layers and the solid state membranes, such as shown in FIGS. 8 and 9. In some embodiments, each graphene layer is comprised of a plurality of discrete graphene strips 82, each of the discrete graphene strips including a plurality of the nanopores 83 extending therethrough. A plurality of the graphene strips are electrically connected to the one or more detectors for detecting tunneling current within the graphene strips. In some embodiments, the graphene strips 82 comprising a first graphene layer have longitudinal axes that extend in a first direction and the graphene strips comprising a second graphene layer have longitudinal axes that extend in a second direction intersecting, and possibly perpendicular to the first direction. FIGS. 8-10 show exemplary embodiments of graphene strips that extend in different directions from layer to layer. The system can further include an electrolyte solution within the nanopores and means (e.g. electrodes connected to an ammeter or other detector that detects ionic current or an electrical parameter convertible to ionic current) for detecting ionic current through the nanopores. The spacing between each graphene layer is less than ten nanometers in one or more embodiments.

An exemplary structure includes a plurality of graphene layers in alternating sequence with and adjoining a plurality of dielectric, solid state membranes 84, each of the graphene layers comprising a plurality of discrete graphene strips 82. A plurality of nanopores 83, 85 extends through the graphene layers and dielectric, solid state membranes. In exemplary embodiments of the structure, as shown in FIGS. 8 and 9, the graphene strips 82 comprising a first graphene layer have longitudinal axes that extend in a first direction and the graphene strips comprising a second graphene layer have longitudinal axes that extend in a second direction perpendicular to the first direction. Each of the graphene strips 82 may include a plurality of nanopores 83 aligned with the nanopores 85 in the dielectric, solid state membranes.

Exemplary System and Article of Manufacture Details

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

One or more embodiments of the invention, or elements thereof, can be implemented in the form of an apparatus including a memory and at least one processor that is coupled to the memory and operative to perform exemplary method steps such as measuring ionic current (both composite and tunneling), creating an electric potential across the receptor-layered passage, applying voltages to graphene electrodes to control the motion of molecules within a nanopore, controlling the mixing of electrolyte solution and potential analyte-containing sample, displaying electrical parameters of interest, and storing data relating to the electrical conductivity within the passage and selected portions of the passage (nanopore). Multiplexed detection of a plurality of materials using arrays on the same device can be facilitated using a processor and memory. Manufacturing steps for making systems capable of performing the techniques disclosed herein can also be controlled through such an apparatus.

Figure 12:
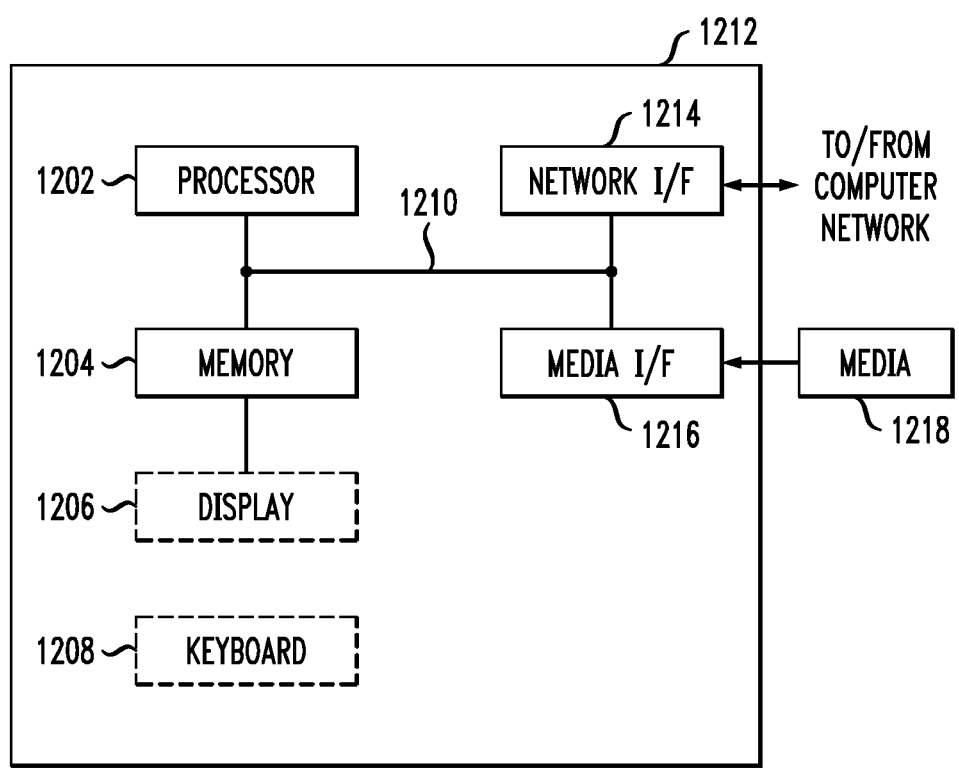
FIG. 12 depicts a computer system that may be useful in implementing one or more aspects and/or elements of the disclosed embodiments.

One or more embodiments can make use of software running on a general purpose computer or workstation. With reference to FIG. 12, such an implementation might employ, for example, a processor 1202, a memory 1204, and an input/output interface formed, for example, by a display 1206 and a keyboard 1208. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU. In addition, the phrase "input/output interface" as used herein, is intended to include, for example, one or more mechanisms for inputting data to the processing unit (for example, mouse), and one or more mechanisms for providing results associated with the processing unit (for example, printer). The processor 1202, memory 1204, and input/output interface such as display 1206 and keyboard 1208 can be interconnected, for example, via bus 1210 as part of a data processing unit 1212. Suitable interconnections, for example via bus 1210, can also be provided to a network interface 1214, such as a network card, which can be provided to interface with a computer network, and to a media interface 1216, such as a diskette or CD-ROM drive, which can be provided to interface with media 1218. Interfaces can be provided to microammeters, valves (not shown) controlling electrolyte solution and sample mixing or flow, and/or current supplies and the like over a network or other suitable interface, analog-to-digital converter, or the like.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 1202 coupled directly or indirectly to memory elements 1204 through a system bus 1210. The memory elements can include local memory employed during actual implementation of the program code, bulk storage, and cache memories which provide temporary storage of at least some program code in order to reduce the number of times code must be retrieved from bulk storage during implementation.

Input/output or I/O devices (including but not limited to keyboards 1208, displays 1206, pointing devices, and the like) can be coupled to the system either directly (such as via bus 1210) or through intervening I/O controllers (omitted for clarity).

Network adapters such as network interface 1214 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 1212 as shown in FIG. 12) running a server program. It will be understood that such a physical server may or may not include a display and keyboard.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method for detecting translocation events associated with a first target molecule while avoiding multiple binding events with respect to the first target molecule, comprising:
    obtaining an assembly including a first graphene sheet bounded by first and second solid-state membranes and a nanopore extending through the graphene sheet and each of the solid-state membranes, the nanopore having an axis, the graphene sheet being positioned at a selected position with respect to the nanopore axis;
    bonding one or more receptors selective to the first target molecule only to the first graphene sheet;
    introducing an electrolyte solution to the nanopore;
    applying an electric potential across the nanopore, and detecting ionic current through the nanopore.

2. The method of claim 1, further including the step of detecting a tunneling current within the graphene sheet.

3. The method of claim 1, further including the step of bonding a plurality of receptors selective to the first target molecule to the graphene sheet.

4. The method of claim 1, wherein only an edge of the graphene sheet is exposed to the nanopore, further including the step of oxidizing the edge of the graphene sheet prior to bonding the one or more receptors.

5. The method of claim 1, wherein the graphene sheet includes a portion protruding into the nanopore.

6. A method for the simultaneous measurement of ionic current through a nanopore and multiple tunneling currents, comprising:
    obtaining an assembly including a plurality of graphene sheets in alternating sequence with a plurality of solid state membranes and a nanopore extending through the graphene sheets and solid state membranes;
    introducing an electrolyte solution to the nanopore;
    applying an electric potential across the nanopore;
    detecting ionic current through the nanopore, and detecting a plurality of tunneling currents within the graphene sheets simultaneously with the step of detecting ionic current through the nanopore.

7. The method of claim 6, further including the step of estimating individual current signals of individual molecules from a combination of the detected ionic current through the nanopore and the detected plurality of tunneling currents.

8. The method of claim 7, wherein the step of estimating individual current signals of individual molecules further includes obtaining tunneling current events from the detected plurality of tunneling currents and analyzing the tunneling current events to obtain molecule translocation currents consistent with both the detected ionic current through the nanopore and the tunneling current events.

9. The method of claim 8, further including the step of selecting a single set of molecule translocation currents based on least variability of at least one criterion.

10. The method of claim 8, wherein the at least one criterion includes molecule speed through the nanopore, magnitude of the tunneling currents, or shape of the tunneling currents.

11. The method of claim 6, further including the step of determining molecular velocity within the nanopore by monitoring the tunneling currents as a function of time.

12. The method of claim 6, further including the step of applying an electric potential to at least one of the graphene layers.

13. The method of claim 6, further including the step of detecting changes in the tunneling currents and using the detected changes in tunneling currents to differentiate at least one of molecular conformations or molecular orientations within the nanopore.

14. The method of claim 6, wherein one or more of the graphene sheets is comprised of a plurality of discrete graphene strips, each of the discrete graphene strips including at least one nanopore extending therethrough, each of the graphene sheets and solid state membranes including a plurality of nanopores, further including the steps of introducing the electrolyte solution to the plurality of nanopores, detecting the ionic current through the plurality of nanopores, and detecting a plurality of tunneling currents within the discrete graphene strips simultaneously with the step of detecting the ionic current through the plurality of nanopores.

15. A system comprising:
   an assembly including a plurality of graphene layers in alternating sequence with a plurality of solid state membranes;
   a plurality of nanopores extending through the graphene layers and the solid state membranes, and
   a plurality of the graphene layers being electrically connected to one or more detectors configured for detecting tunneling currents within the graphene layers associated with charged molecules within the nanopores.

16. The system of claim 15, wherein each graphene layer is comprised of a plurality of discrete graphene strips, each of the discrete graphene strips including a plurality of the nanopores extending therethrough, a plurality of the graphene strips being electrically connected to the one or more detectors.

17. The system of claim 16, wherein the graphene strips comprising a first of the graphene layers have longitudinal axes that extend in a first direction and the graphene strips comprising a second of the graphene layers have longitudinal axes that extend in a second direction intersecting the first direction, one or more of the graphene strips comprising the first graphene layer overlapping one or more of the graphene strips comprising the second graphene layer.

18. The system of claim 16, wherein one or more of the graphene strips comprising a first of the graphene layers overlap at least two of the graphene strips comprising a second of the graphene layers.

19. The system of claim 16, further including electrolyte within the nanopores and means for detecting ionic current through the nanopores.

* * * * *